United States Patent [19]

Proctor et al.

[11] Patent Number: 4,694,165

[45] Date of Patent: Sep. 15, 1987

[54] BULK MATERIAL ANALYZER CALIBRATION BLOCK

[75] Inventors: Raymond J. Proctor, San Diego; Thomas L. Atwell, Del Mar; Clinton L. Lingren, San Diego; James F. Miller, Solana Beach, all of Calif.

[73] Assignee: Gamma-Metrics, San Diego, Calif.

[21] Appl. No.: 782,272

[22] Filed: Sep. 30, 1985

[51] Int. Cl.$^4$ ...................... G01D 18/00; G01F 23/00
[52] U.S. Cl. .............................. 250/252.1; 250/359.1; 250/505.1
[58] Field of Search ............... 250/252.1, 359.1, 505.1; 378/207; 424/4

[56] References Cited

U.S. PATENT DOCUMENTS

| | | | |
|---|---|---|---|
| 3,031,575 | 4/1962 | Gevantman et al. | 250/252.1 |
| 3,205,355 | 9/1965 | Ehlert | 250/83 |
| 3,334,233 | 8/1967 | Veal | 250/106 |
| 3,435,215 | 3/1969 | Pritchett | 250/83 |
| 3,867,638 | 2/1975 | Golden | 250/505 |
| 3,935,449 | 1/1976 | Reunanen | 250/252 |
| 4,047,032 | 9/1977 | Judge et al. | 250/338 |
| 4,082,950 | 4/1978 | Chen | 250/343 |
| 4,095,105 | 6/1978 | Rosenthal | 250/338 |
| 4,152,600 | 5/1979 | Berry | 250/505 |
| 4,266,132 | 5/1981 | Marshall, III | 250/359.1 |
| 4,314,155 | 2/1982 | Sowerby | 250/253 |
| 4,499,375 | 2/1985 | Jaszczak | 250/252.1 |
| 4,582,992 | 4/1986 | Atwell et al. | 250/359.1 |

OTHER PUBLICATIONS

Coal Handbook; Meyers (Ed.), Dekker, New York, 1981, pp. 19-74.

Stewart et al.; Bureau of Mines, Technical Progress Report 74, 1974.
Duffey et al.; American Nuclear Society Transactions, Winter 1976, vol. 24, pp. 117-118.
Brown et al.; Nuclear Assay of Coal, vol. 10, EPRI Document RP983-4, Nov. 1983.

Primary Examiner—Janice A. Howell
Attorney, Agent, or Firm—Edward W. Callan

[57] ABSTRACT

A calibration block is used for calibrating a bulk material analyzer that has an activation region in which bulk material is received for analysis and a chute for passing the bulk material through the activation region. The block is dimensioned to be of almost the same cross-sectional size as the interior of the chute and extends both above and below the activation region when inserted in the chute. The calibration block is manufactured by (a) providing a mixture of known materials of known proportions that do not chemically react with each other, including a bonding agent; (b) homogenizing the mixture to make a thick paste in which the known materials are bound without segregation of known materials that have different densities; (c) molding the homogeneous mixture into the shape of a block having predetermined dimensions; and (d) solidifying the molded mixture to provide the calibration block. Alternative processes for manufacturing the calibration block utilize compaction and sintering techniques instead of a bonding agent. The measurement system of the bulk material analyzer is calibrated in accordance with measurements made while the calibration block is in the chute. One embodiment of the calibration block includes a plurality of uniformly distributed holes extending through the block for receiving insertions of a known quantity of a unique known material.

9 Claims, 6 Drawing Figures

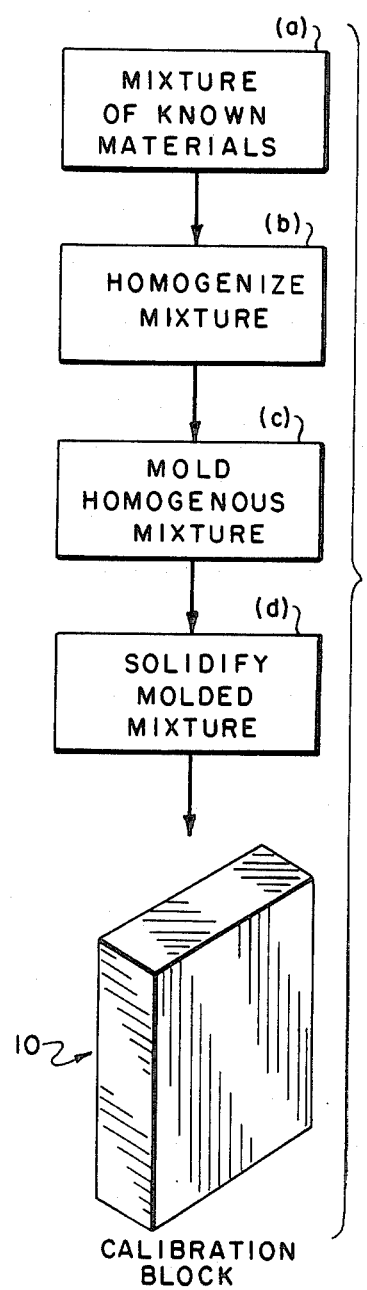
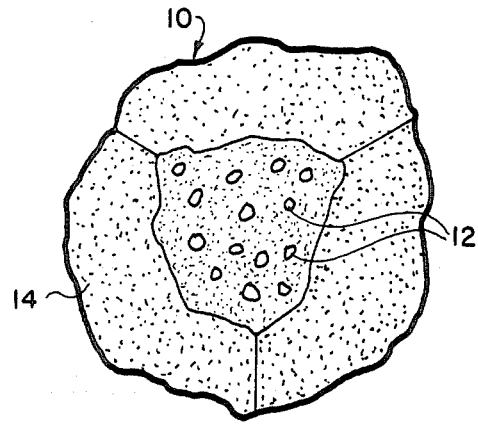
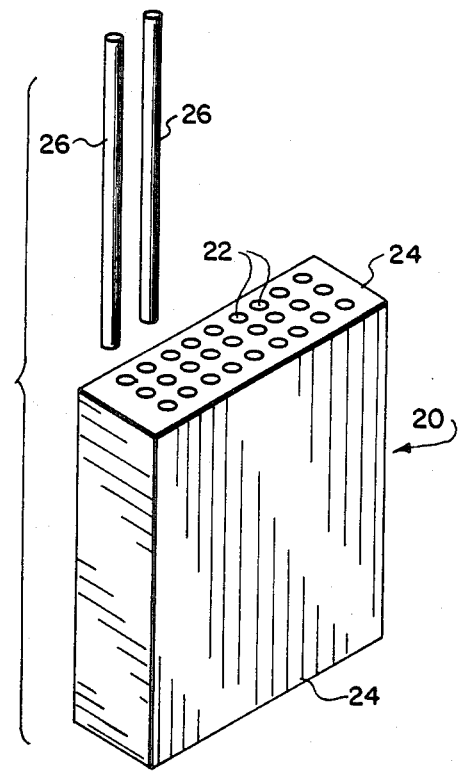
FIG. 1
FIG. 2
FIG. 3

BULK MATERIAL ANALYZER CALIBRATION BLOCK

BACKGROUND OF THE INVENTION

The present invention generally pertains to calibration of a bulk material analyzer and is particularly directed to the composition, use and manufacture of a calibration block for a bulk material analyzer.

Bulk material analyzers are used to measure the elemental content of bulk material. Such analyzers have been developed primarily to measure the quantitative content of materials, such as ash, in batches of coal. The parameters of interest may be determined from the measurement of the elemental content of the bulk materials.

In a typical prior art bulk material analyzer, the bulk material is transported through an activation region between a radiation source and a gamma ray detector, and the detector produces signals which are processed to provide a measurement of the elemental content of the bulk material. Typically the radiation source is a neutron source. When the bulk material absorbs neutrons, secondary emissions of gamma rays are produced from the bulk material. Different characteristic gamma ray energy spectra are produced from different elements in the bulk materials. Accordingly, by processing detected signals that are indicative of the gamma ray spectrum, a measurement is provided of the elemental content of the bulk material. This measurement process is known in the art as prompt gamma ray neutron activation analysis (PGNAA).

In the prior art, bulk material analyzers have been calibrated by using samples of materials of the type that are to be analyzed. Prior to calibration, the samples are subjected to laboratory analysis to determine their elemental content. Typically, the samples used in the chemical laboratory analysis are relatively small compared to the quantity of bulk material present in the activation region during operation of the bulk material analyzer. For example, whereas a coal analyzer typically has several hundred pounds of coal in its activation region during operation, a coal analysis laboratory uses only 50 grams (0.1 pounds) or less of finely crushed coal, from which it draws sub-samples for each of the necessary chemical analyses. Coal is a heterogeneous material. Hence, a major source of inaccuracy in any coal analysis is the collection of the sample of 0.1 pounds (50 grams) that is truly representative of several hundred pounds of bulk coal. According to the Coal Handbook, Meyers (Ed.), Dekker, New York, 1981 uncertainties in obtaining and preparing the sample are twenty times greater than a laboratory's analytical uncertainty.

Since the first development of large scale PGNAA coal analyzers a quick, easy and accurate method of calibration has been a problem. Over the past ten years published research from the Electric Power and Research Institute (EPRI) has identified the calibration problems and attempted to solve them by several different methods.

One such prior art method includes the step of uniformly and accurately "spiking" moving coal streams with elements and compounds. This method is described by R. F. Stewart et al.; Bureau of Mines Tech. Progress Report 74, 1984. This method requires a mechanical means to move the coal dynamically for even mixing. Only one element can be done at a time and once a coal has been spiked the coal must be discarded or re-used in its contaminated form. Segregation of the coal and spike material can give large inaccuracies. This method is not particularly easy, quick or accurate.

Another prior art method includes the step of mixing up a powdered plastic, or a carbohydrate sugar, and dry chemical compounds to simulate a coal matrix and thereby provide a standard material. This method is described by Duffey et al.; American Nuclear Society Transactions, Winter 1976; Vol. 24, p. 117. Using this method, different elemental coal types can be simulated. However, it is physically difficult to achieve controllable densities with powders. Contamination, especially from moisture, can easily occur. Hence, care is needed in using, handling and storing the standards. Even the most elaborate of blending methods cannot overcome the problems of segregation between lighter and heavier material components. Segregation gives inaccuracy. This method is quick but not accurate nor easy.

Still another prior art calibration method uses boxes of powdered coal that have been heavily sampled and then analyzed by many (3-5) laboratories and thus are assumed to be "standard materials." This method is described by Brown, Gozani & Spencer; Nuclear Assay of Coal, Vol. 10, EPRI Document RP, pp. 983-4, Nov. 1983. In this method, the box is analyzed simultaneously with the "standard material". The box thus represents a non-uniformly distributed contaminant to the "standard material". The density and freedom from segregation cannot be maintained upon transport and handling. Also, it is doubtful whether the "standard materials" will remain stable in density and moisture distribution over long periods of time when they are not hermetically sealed. This method is quick and easy, but its accuracy does not allow a calibration that will test a PGNAA bulk material analyzer to its limits.

SUMMARY OF THE INVENTION

The present invention provides a calibration block for use in calibrating a bulk material analyzer. The calibration block of the present invention is a block of a solidified homogeneous mixture of known materials in known proportions, wherein the materials do not react chemically with one another. In the preferred embodiment, the known materials are standard technical grade chemicals that have been laboratory analyzed for all of their constituent elements. Typically, the known materials and their proportions are selected to provide a calibration block having a proportionate elemental composition that is typical of the bulk material that is to be analyzed.

A preferred embodiment of the calibration block is useful in calibrating a bulk material analyzer that has an activation region in which bulk material is received for analysis and a chute for passing the bulk material through the activation region. In such embodiment, the calibration block is dimensioned to be of almost the same lateral cross-sectional size as the bulk material passage through the activation region. This feature coupled with the homogeneous character of the calibration block prevents the calibration from being affected by any spatial dependence of the bulk material analyzer upon the lateral distribution of the material within the activation region.

In a separate aspect, the present invention provides a process of manufacturing a calibration block. Such process includes the steps of (a) providing a mixture of known materials of known proportions that do not chemically react with each other, including a bonding agent; (b) homogenizing the mixture to make a thick paste in which the bonding agent binds the other known materials and prevents segregation of known materials that have different densities; (c) molding the homogenous mixture into the shape of a block having predetermined dimensions; and (d) solidifying the molded mixture to provide a solid calibration block.

The preferred bonding agent is polyester resin, which is a relatively simple homogeneous chemical that can be well characterized as to its proportionate elemental composition. The density of polyester resin is approximately 1.3 to 1.4 grams/cc, whereas coal typically has a bulk density of 0.8 to 1.0 grams/cc. In order to reduce the density of the calibration block to be comparable to that of the material that is to be analyzed, one of the known materials of the mixture is chosen to be microspheres. Microspheres are small bubbles. The use of phenolic microspheres, which have an elemental composition of carbon, hydrogen and oxygen, enables the calibration block to be tailored by judicious choice of the other carbon, hydrogen and oxygen containing materials to be of a predetermined density without severely impacting the overall elemental composition of the calibration block. In this regard, it is noted that the PGNAA measurement technique is insensitive to oxygen.

In further aspects, the present invention provides alternative processes of manufacturing a calibration block that include the techniques of compaction and sintering. One such process includes the steps of (a) providing a mixture of known materials of known proportions that do not chemically react with each other; (b) homogenizing the mixture; (c) filling a shell of predetermined dimensions with the homogenous mixture by incrementally compacting the homogenous mixture in the shell in layers that are of such depth as to attain uniform compaction density throughout the shell and as to prevent substantial segregation of known materials that have different densities; and (d) sealing the shell to provide the calibration block.

The other alternative process of manufacturing a calibration block, includes the steps of (a) providing a mixture of known materials of known proportions that do not chemically react with each other; (b) homogenizing the mixture; (c) filling a mold of predetermined dimensions with the homogenous mixture by incrementally compacting the homogenous mixture in the mold in layers that are of such depth as to attain uniform compaction density throughout the mold and as to prevent substantial segregation of known materials that have different densities; and (d) sintering the molded mixture to provide the calibration block.

The calibration block of the present invention is used in a method of calibrating a bulk material analyzer that has an activation region in which bulk material is received for analysis and measurement means for measuring the elemental content of the received bulk material. Such method includes the steps of (a) inserting within the activation region a calibration block that includes a block of a solidified homogeneous mixture of known materials in known proportions, wherein the materials do not react chemically with one another; (b) taking measurements with the bulk material analyzer while the calibration block is within the activation region; and (c) calibrating the measurement means in response to the measurements taken in step (b) in accordance with the known proportions of the known materials of the calibration block.

Such method is useful for calibrating a bulk material analyzer having a chute for passing the bulk material through the activation region. In accordance with such method, the calibration block that is used is dimensioned to be of almost the same lateral cross-sectional size as the interior of the chute.

In a preferred embodiment, the calibration block that is used is longer than the dimension of the activation region through which the bulk material passes in order to simulate a continuous flow of bulk material through the activation region.

One preferred embodiment of the calibration block contains a plurality of holes. A known quantity of a unique known material is inserted in one or more of the holes to measure the sensitivity of the bulk material analyzer to that unique known material, or to measure the spatial variance of the sensitivity of the bulk material analyzer in accordance with the measurements obtained for the inserted unique known material.

Additional features of the present invention are discussed in relation to the description of the preferred embodiments.

BRIEF DESCRIPTION OF THE DRAWINGS

FIG. 1 combines a block diagram of the manufacturing process of the present invention that utilizes a bonding agent with a perspective view of one preferred embodiment of a calibration block according to the present invention.

FIG. 2 is a greatly enlarged view of a portion of the calibration block of FIG. 1, with a portion cut away to illustrate the uniform distribution of the known materials therein.

FIG. 3 is a perspective view of an alternative embodiment of the calibration block of the present invention.

DESCRIPTION OF THE PREFERRED EMBODIMENTS

Figure 4:
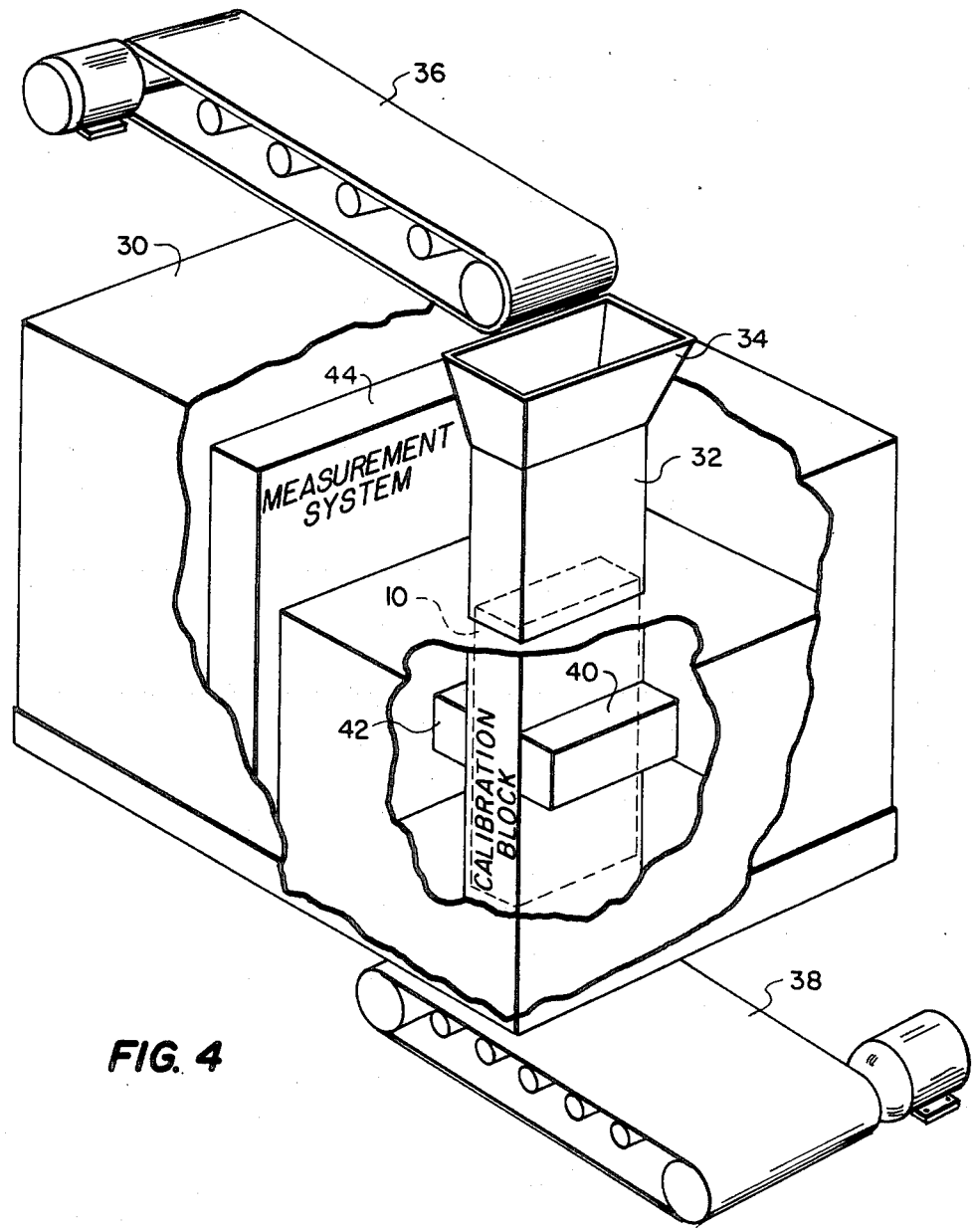
FIG. 4 is a perspective view, with portions cut away, of a bulk material analyzer in which the calibration block of the present invention has been installed for calibration of the analyzer.

The process of manufacturing a calibration block in accordance with the present invention is described with reference to FIG. 1. The first step (a) is to provide a mixture of known materials of known proportions that do not chemically react with each other, including a polyester resin. The next step (b) is to homogenize the mixture to make a thick paste in which the resin binds the other known materials and prevents segregation of the other known materials that have different densities. Accordingly, the lighter materials of the mixture are not segregated from the heavier components once the mixture has been homogenized. The third step (c) is to mold the homogenous mixture into the shape of a block having predetermined dimensions. The final step (d) is to solidify the molded mixture to provide a solid calibration block 10. The mold is then removed so that the calibration block 10 can be used.

The known components are all standard technical grade chemicals that have been laboratory analyzed for all of their constituent elements. Typically, the known materials and their proportions are selected to provide a calibration block having a proportionate elemental composition that is typical of the bulk material that is to be analyzed. The basic composition of the calibration block 10 can be tailored by variation of the proportions of the constituent known materials to vary the proportions of a plurality of the constituent elements simultaneously.

The following examples describe the composition of a calibration block that has been manufactured for use in calibrating a bulk material analyzer for measurements of the elemental content of different types of western coal:

EXAMPLE 1

(Western)

TABLE 1

| Material | Weight Percent |
|---|---|
| polyester resin | 68.000 |
| methylethyl ketone peroxide (hardener) | 1.360 |
| anhydrous magnesium sulfate | 3.500 |
| iron oxide | 0.600 |
| silicon dioxide | 3.000 |
| calcium carbonate | 3.500 |
| alumina | 2.400 |
| Sodium carbonate | 0.250 |
| Nylon 6/6 | 7.260 |
| titanium dioxide | 0.075 |
| potassium chloride | 0.050 |
| boron | 0.005 |
| phenolic microspheres | 10.000 |

The elemental breakdown for the calibration block of Example 1 is as follows:

TABLE 2

| Element | Weight Percent |
|---|---|
| Hydrogen | 5.761 |
| Boron | 0.005 |
| Carbon | 60.268 |
| Nitrogen | 0.941 |
| Oxygen | 27.573 |
| Sodium | 0.329 |
| Magnesium | 0.449 |
| Aluminum | 0.769 |
| Silicon | 1.399 |
| Sulfur | 0.643 |
| Chlorine | 0.029 |
| Potassium | 0.027 |
| Calcium | 1.358 |
| Titanium | 0.045 |
| Iron | 0.405 |

EXAMPLE 2

(western, 24% ash, high density)

TABLE 3

| Material | Weight Percent |
|---|---|
| polyester S40 | 58.000 |
| methylethyl ketone peroxide (hardener) | 1.160 |
| dry magnesium sulfate | 6.500 |
| black iron oxide | 1.800 |
| silicon dioxide | 12.500 |
| calcium carbonate | 5.460 |
| alumina | 7.100 |
| sodium carbonate | 0.250 |
| titanium dioxide | 0.075 |
| potassium chloride | 0.050 |
| boron | 0.0046 |

TABLE 3-continued

| Material | Weight Percent |
|---|---|
| phenolic microspheres | 7.000 |

The elemental breakdown for the calibration block of Example 2 is as follows:

TABLE 4

| Element | Weight Percent |
|---|---|
| Hydrogen | 4.751 |
| Boron | 0.0045 |
| Carbon | 46.844 |
| Nitrogen | 0.076 |
| Oxygen | 34.522 |
| Sodium | 0.271 |
| Magnesium | 0.831 |
| Aluminum | 2.299 |
| Sulfur | 1.193 |
| Silicon | 5.787 |
| Chlorine | 0.036 |
| Potassium | 0.027 |
| Calcium | 2.109 |
| Titanium | 0.046 |
| Iron | 1.204 |

EXAMPLE 3

(western, medium density, low hydrogen)

TABLE 5

| Material | Weight Percent |
|---|---|
| polyester S40 | 58.000 |
| methylethyl ketone peroxide (hardener) | 1.160 |
| dry magnesium sulfate | 3.500 |
| black iron oxide | 0.600 |
| silicon dioxide | 3.000 |
| calcium carbonate | 3.500 |
| alumina | 2.400 |
| sodium carbonate | 0.250 |
| titanium dioxide | 0.075 |
| potassium chloride | 0.050 |
| boron | 0.005 |
| phenolic microspheres | 10.000 |
| graphite | 16.090 |
| polyethylene | 1.370 |

The elemental breakdown for the calibration block of Example 3 is as follows:

TABLE 6

| Element | Weight Percent |
|---|---|
| Hydrogen | 4.724 |
| Boron | 0.0045 |
| Carbon | 62.922 |
| Nitrogen | 0.443 |
| Oxygen | 25.137 |
| Sodium | 0.352 |
| Magnesium | 0.468 |
| Aluminum | 1.027 |
| Sulfur | 0.693 |
| Silicon | 2.020 |
| Chlorine | 0.034 |
| Potassium | 0.091 |
| Calcium | 1.482 |
| Titanium | 0.052 |
| Iron | 0.549 |

In these calibration blocks, the elementally simple polyester resin is the major constituent of the homogenized mixture. The proportion of each of the minor constituent materials of the mixture is not more than twenty percent. Hence, any laboratory analysis uncertainties associated with the minor constituent materials are reduced by a factor of five or greater when applied to the constituents of the entire calibration block.

In one preferred embodiment, as shown in FIG. 1, the calibration block 10 is a solid block. The density of the block is determined in accordance with the proportion of microspheres included in the mixture. Preferably, the microspheres are small, phenolic plastic bubbles which are 50 microns in diameter, with 1 micron thick shells. FIG. 2 illustrates the uniform distribution of the microspheres 12 in the solidified homogenized mixture 14 of the calibration block 10. The calibration block 10 is of rugged one-piece construction for ease of handling.

The calibration block 10 has a consistent concentration of constituent materials per unit volume. The materials chosen for the calibration block are both chemically and biologically stable for a long term period of several years. Hence, the calibration block is dimensionally stable.

An alternative preferred embodiment of a calibration block 20 according to the present invention is shown in FIG. 3. The calibration block 20 includes a plurality of uniformly distributed holes 22 that extend between the ends 24 of the calibration block. The holes 22 are created either by drilling through the calibration block 20 or by molding the homogeneous mixture with a mold that defines the holes 22 in the molded calibration block 20. In other respects the calibration block 20 is manufactured in the same manner as the calibration block 10 described above with reference FIGS. 1 and 2.

In an embodiment, wherein the calibration block 20 has an exterior rectangular solid shape, as shown in FIG. 3, and is dimensioned to be approximately 1 foot (30 cm) by 3 (91 cm) feet by 5 feet (152 cm), there are twenty-seven holes in a three-by-nine matrix, with the centers of the holes being separated by four inches (10 cm) and the edges of the peripheral holes being two inches (5 cm) from the adjacent edges of the end surfaces 24 of the block 20. The holes have a ¾ inch (1.9 cm) diameter. Tubes 26 are provided for insertion in the holes 22. The tubes 26 are hollow aluminum tubes of ⅝ inch (1.6 cm) external diameter. The tubes 26 are filled with a unique known material and inserted into the holes 22 of the block 20.

The preferred embodiments of the calibration blocks described with reference to FIGS. 1 and 3 are dimensioned for use in calibrating the type of bulk material analyzer that is described in U.S. patent application No. 639,577, filed Aug. 10, 1984 for "Self-Contained, On-Line, Real-Time, Bulk Material Analyzer" by Thomas L. Atwell et al., now U.S. Pat. No. 4,582,992 which is commonly assigned with the present application, and the pertinent disclosure of which is incorporated herein by reference thereto. Such a bulk material analyzer is shown in FIG. 4.

The bulk material analyzer includes a portable container 30. The container is approximately eight feet (244 cm) wide by ten feet (305 cm) long by eight feet (244 cm) high. The dimensions stated herein are particularly applicable to a coal analyzer and may differ for analyzers of other types of bulk materials in accordance with the physical characteristics of the bulk material, such as flowability.

An open-ended vertical chute 32 extends through the container 30. An input hopper 34 is fastened to the top of the chute 32 for receiving bulk material that is channeled through the chute 32. The bulk material (not shown), such as coal, is fed into the hopper 34 by an input conveyor 36 and is fed away from the bottom of the chute 32 by an output conveyor 38.

The chute 32 is particularly dimensioned in accordance with the flow characteristics of the bulk material; and for application to coal thereby has an interior rectangular cross section of approximately one foot (30 cm) by three feet (91 cm) to assure that coal which is up to 4-inch (10 cm) top size will flow therethrough without plugging or bridging within the chute 32. The chute 32 is approximately eight feet (244 cm) long.

Neutron radiation sources 40 are symmetrically disposed on and outside one of the three-foot (91 cm) long sides of chute 32. The sources 40 are adjacent to the three-foot (91 cm) long sides of the chute 32.

Gamma ray detectors 42 are symmetrically disposed on and outside the other of the three-foot (91 cm) long sides of the chute opposing the positions of the neutron sources 40 on the one side of the chute 32.

The sources 40 and the detectors 42 are aligned in a common plane which is approximately three feet (91 cm) above the bottom of the chute 32. The region generally between and extending above and below past the sources 40 and the detectors 42 is referred to herein as the activation region. In the analyzer shown in FIG. 4, the activation region is approximately two feet (61 cm) long in the longitudinal dimension of the chute 32.

The detectors 42 detect gamma rays that are secondarily emitted by materials in the activation region that are bombarded by neutron radiation from the sources 40. The detectors 42 produce signals in response to the detected gamma rays. These produced signals are characteristic of the elemental content of the bulk material in the activation region.

The sources 40 and detectors 42 are relatively disposed as described above for causing the measurements to be independent of the lateral distribution of the bulk material in the chute 32.

The bulk material analyzer further includes a measurement system 44 for combining and processing the signals produced by the detectors 42 to provide a measurement of the elemental content of the bulk material that is channeled through the activation region by the chute 32.

The calibration block 10, 20 is dimensioned to be of almost the same lateral cross-sectional size as the interior of the chute 32, being only slightly smaller so that it 10,20 can be inserted into the chute 32. FIG. 4 shows a calibration block 10 (dashed lines) inserted within the chute 32. The calibration block 10 is longer than the activation region. In the embodiment of FIG. 4, the calibration block is five feet (152 cm) long and extends both above and below the two-foot (61 cm) long activation region when inserted in the chute 32 for calibrating the bulk material analyzer. The calibration block 10 thereby simulates the continuous flow of bulk material through the activation region.

The following method is employed to calibrate the bulk material analyzer of FIG. 4 with the calibration block 10. The calibration block 10 is inserted into the chute 32, as shown in FIG. 4 and described above. Next, measurements of elemental content are taken by the measurement system 44 for all of the elements in the calibration block 10 while the calibration block 10 is in the chute 32. Finally, the measurement system 44 is calibrated in response to the measurements taken while the calibration block 10 is in the chute 32 in accordance with the known proportions of the known materials of the calibration block 10.

The calibration block 20 having the holes 22 extending therethrough is used in two alternative embodiments of the method of calibrating the bulk material analyzer of FIG. 4. In one such alternative embodiment, each of the tubes 26 is filled with a known quantity of a unique known material, the tubes 26 are placed in all of the holes 22 and measurements are made with the measurement system 44. The measurements system 44 is then calibrated in accordance with such measurements so that the bulk material analyzer can make accurate measurements of the elemental content of such unique known material when it is present in the type of bulk material simulated by the integral portion of the calibration block 20. In these embodiments measurements are also made with empty tubes 26 inserted in the same manner as the filled tubes in order to account for the composition of the tubes 26.

In the other such alternative embodiment using the calibration block 20, the bulk material analyzer is calibrated for variations in its spatial sensitivity. In this embodiment, only one of the tubes 26 is filled with a unique known material. This tube 26 is inserted in only one of the holes 22 at a time, but is sequentially inserted in each of the holes 22. While the tube 26 is in each hole 22, measurements are taken of the elemental content of the unique known material. These measurements provide an indication of the sensitivity of the bulk material analyzer to lateral variations of the position of the unique known material. The sensitivity of the bulk material analyzer to vertical variations of the position of the unique known material is determined by inserting a small slug in the one tube 26 and by varying the depth of insertion of the slug into the activation region for each of the holes 22 of the calibration block, with a measurement being taken for each depth of insertion for each hole 22 to provide a complete three-dimensional profile of the spatial sensitivity of the bulk material analyzer. These measurements are then used to refine the calibration of the measurement system.

Alternative to the use of a slug at varied depths, a tube 26 is partially filled to a given depth with a unique known material and such depth is varied as the measurements are taken to obtain the three-dimensional profile.

Figure 5:
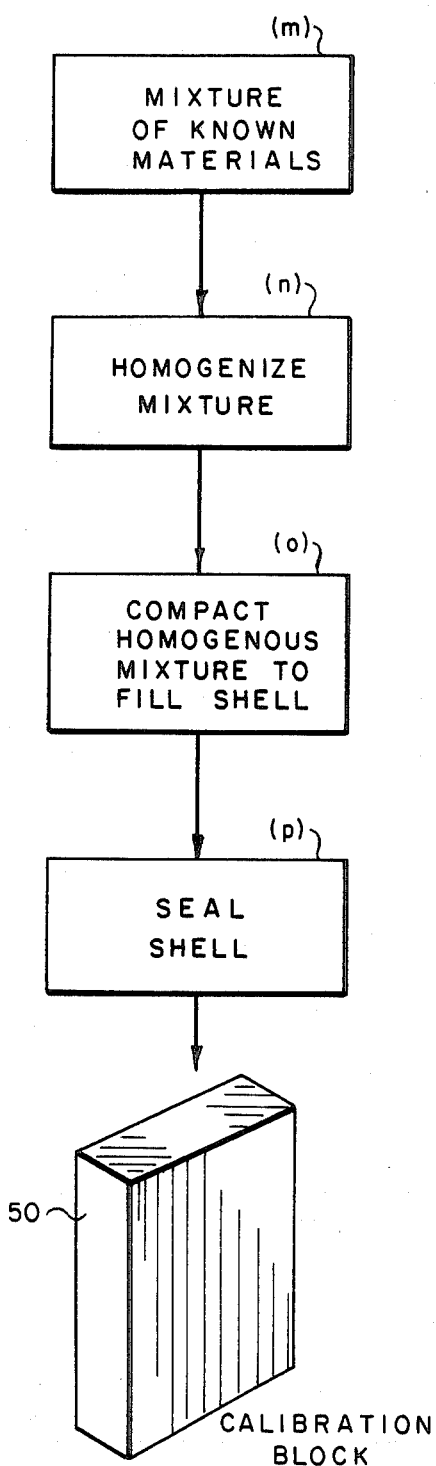
FIG. 5 is a block diagram of a manufacturing process according to the present invention that utilizes a compaction technique.

FIG. 5 shows a process of manufacturing a calibration block according to the present invention that utilizes a compaction technique. The first step (m) is to provide a mixture of known materials of known proportions that do not chemically react with each other. The next step (n) is to homogenize the mixture. The third step (o) is to fill a shell of predetermined dimensions with the homogenous mixture by incrementally compacting the homogenous mixture in the shell in layers that are of such depth as to attain uniform compaction density throughout the shell and as to prevent substantial segregation of known materials that have different densities. The final step (p) is seal the shell to provide the calibration block 50. The shell forms the outer skin of the calibration block 50.

Figure 6:
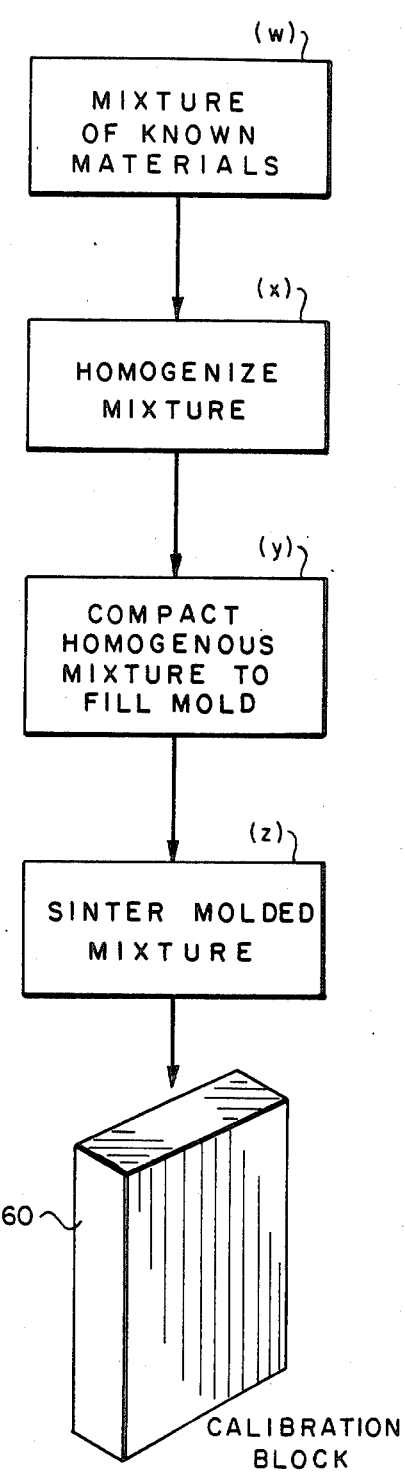
FIG. 6 is a block diagram of the manufacturing process of the present invention that utilizes a sintering technique.

FIG. 6 shows a process of manufacturing a calibration block according to the present invention that utilizes a sintering technique. The first step (w) is to provide a mixture of known materials of known proportions that do not chemically react with each other. The next step (x) is to homogenize the mixture. The third step (y) is to fill a mold of predetermined dimensions with the homogenous mixture by incrementally compacting the homogenous mixture in the mold in layers that are of such depth as to attain uniform compaction density throughout the mold and as to prevent substantial segregation of known materials that have different densities. The final step (z) is sinter the molded mixture to provide the calibration block 60. The mold is then removed so that the calibration block 60 can be used.

For both of the processes of FIGS. 5 and 6, the known components are all standard technical grade chemicals that have been laboratory analyzed for all of their constituent elements. These two processes provide the advantage of not having to utilize a bonding agent, when the bonding agent includes elements that are not desired in the calibration block.

The following example describes the composition of a calibration block that has been manufactured according to the process of FIG. 5 for use in calibrating a bulk material analyzer for measurements of the content of a given type of cement.

EXAMPLE 4
TABLE 7

| Material | Weight Percent |
|---|---|
| silicon dioxide | 13.70 |
| alumina | 2.39 |
| ferric oxide | 2.33 |
| calcium carbonate | 75.64 |
| magnesium carbonate | 5.94 |

For this example, the mixture was incrementally compacted in layers that were approximately one inch (2.5 cm) deep.

The calibration blocks 50, 60 manufactured by the processes of FIGS. 5 and 6 are used to calibrate a bulk material analyzer in the same manner as with the calibration block 10 described hereinabove.

For ease of handling, a plurality of identically constituted small calibration blocks (not shown) may be used in lieu of one large calibration block.

Also, although a rectangular shape is preferred for a calibration block used in a chute having a rectangular horizontal cross-section, such as in the bulk material analyzer of FIG. 1; alternatively, a plurality of indentically constituted spherical calibration blocks (not shown) can be used. The spherical blocks are poured into the chute 12 up to a level above the activation region and the calibration measurements are taken in the same manner as with the large singular calibration block 26. Spherical calibration blocks are preferred over the rectangular cross-section calibration blocks when the chute of the bulk material analyzer has a rounded horizontal cross section.

What is claimed is:

1. A calibration block for use in calibrating a bulk material analyzer, comprising
   a block of a solidified homogeneous mixture of known materials in known proportions, wherein the materials do not react chemically with one another.

2. A calibration block according to claim 1 for use in a bulk material analyzer having an activation region in which bulk material is received for analysis and means for passing the bulk material through the activation region,
   wherein the block is dimensioned to be of almost the same lateral cross-sectional size as the bulk material passage through the activation region.

3. A calibration block according to claim 2 that is longer than the dimension of the activation region through which the bulk material passes.

4. A calibration block according to claim 1, wherein the known materials include a bonding agent that binds the other known materials and prevents segregation of known materials that have different densities.

5. A calibration block according to claim 4, wherein the known materials include microspheres.

6. A calibration block according to claim 1, wherein the known materials include microspheres.

7. A calibration block according to claim 1, wherein the known materials include phenolic microspheres.

8. A calibration block according to claim 1 containing a plurality of holes for receiving inserts of known materials.

9. A calibration block according to claim 8 having a known quantity of a unique known material inserted in one or more of said holes.

* * * * *